(12) United States Patent
Martin et al.

(10) Patent No.: US 11,127,486 B2
(45) Date of Patent: Sep. 21, 2021

(54) SYSTEMS AND METHODS FOR PREDICTING A SMOKING STATUS OF AN INDIVIDUAL

(71) Applicant: Philip Morris Products S.A., Neuchâtel (CH)

(72) Inventors: Florian Martin, Peseux (CH); Marja Talikka, Orbe (CH)

(73) Assignee: Philip Morris Products S.A., Neuchâtel (CH)

( * ) Notice: Subject to any disclaimer, the term of this patent is extended or adjusted under 35 U.S.C. 154(b) by 579 days.

(21) Appl. No.: 15/104,414

(22) PCT Filed: Dec. 11, 2014

(86) PCT No.: PCT/EP2014/077473
§ 371 (c)(1),
(2) Date: Jun. 14, 2016

(87) PCT Pub. No.: WO2015/091255
PCT Pub. Date: Jun. 25, 2015

(65) Prior Publication Data
US 2016/0314244 A1 Oct. 27, 2016

Related U.S. Application Data

(60) Provisional application No. 61/916,443, filed on Dec. 16, 2013.

(51) Int. Cl.
*G16B 40/00* (2019.01)
*G16B 20/00* (2019.01)
*C12Q 1/6876* (2018.01)
*G06N 7/00* (2006.01)

(52) U.S. Cl.
CPC .......... *G16B 40/00* (2019.02); *C12Q 1/6876* (2013.01); *G06N 7/005* (2013.01); *G16B 20/00* (2019.02); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,718,946 B2 | 5/2014 | Bevilacqua et al. | |
| 2007/0099209 A1* | 5/2007 | Clarke | C12Q 1/6886 435/6.12 |
| 2007/0254369 A1 | 11/2007 | Grimes et al. | |
| 2010/0119474 A1 | 5/2010 | Crystal et al. | |
| 2011/0256545 A1 | 10/2011 | Guo et al. | |
| 2012/0171158 A1 | 7/2012 | Albert et al. | |
| 2013/0288988 A1 | 10/2013 | Cartwright et al. | |
| 2014/0060552 A1* | 3/2014 | Cohen | G16H 20/70 131/273 |
| 2014/0246036 A1* | 9/2014 | Qu | C12N 15/8243 131/352 |

FOREIGN PATENT DOCUMENTS

| | | |
|---|---|---|
| CN | 1612936 A | 5/2005 |
| CN | 101479599 A | 7/2009 |
| JP | 2003-500715 A | 1/2003 |
| WO | WO 00/71756 A2 | 11/2000 |
| WO | WO 2013/032917 | 3/2013 |
| WO | WO 2013/067040 A1 | 5/2013 |

OTHER PUBLICATIONS

Webb, A. R. Statistical Pattern Recognition, Second Edition; John Wiley & Sons, Ltd.: Chichester, UK, 2002. excerpt of pp. 145-148.*
Beineke et al., "A whole blood gene expression-based signature for smoking status," BMC Med Genomics, p. 58 (2012) (10 pages).
Verdugo et al., "Graphical modeling of gene expression in monocytes suggests molecular mechanisms explaining increased atherosclerosis in smokers," PLoS One, 8:(1)e50888 (2013).
"Array-Based Gene Expression Analysis," www.illumia.com Apr. 10, 2013 URL:https://web.archive.org/web/2013041 0192832/http:/1 www.illumina.com/documents/products/datasheets/datasheet_gene_exp_analysis.pdf [retrieved on May 8, 2015].
International Search Report and Written Opinion of PCT/EP2014/077473 dated May 11, 2015.
Bahr et al, "Peripheral Blood Mononuclear Cell Gene Expression in Chronic Obstructive Pulmonary Disease", Gene Expression Signatures in COPD, American Journal of Respiratory Cell and Molecular Biology, vol. 49, pp. 316-323, 2013.
Brettschneider et al., "Quality assessment for short oligonucleotide microarray data", arXiv:0710.0178v2 [stat.ME] Nov 16, 2007, pp. 1-44.
Dumeaux et al., "Deciphering Normal Blood Gene Expression Variation—The NOWAC Postgenome Study", PLOS Genetics, vol. 6, Issue 3, e1000873, Mar. 12, 2010, pp. 1-11.
Gautier et al., "Affy-analysis of Affymetrix GeneChip data at the probe level", Bioinformatics, vol. 20, No. 3, 2004, pp. 307-315, DOI: 10.1093/bioinformatics/btg405.
Gentlemen et al., "Bioconductor: open software development for computational biology and bioinformatics", Genome Biology, vol. 5, Issue 10, Article R80, Sep. 15, 2004, pp. 1-16.
Irizarry et al., "Exploration, normalization, and summaries of high density oligonucleotide array probe level data", Biostatics (2003), vol. 4, Issue 2, pp. 249-264.

(Continued)

*Primary Examiner* — Soren Harward
(74) *Attorney, Agent, or Firm* — Sterne, Kessler, Goldstein & Fox P.L.L.C.

(57) ABSTRACT

Systems and methods are provided for assessing a sample obtained from a subject. The computerized method includes receiving, by receiving circuitry, a dataset associated with the sample, the dataset comprising quantitative expression data for LRRN3, CDKN1C, PALLD, SASH1, RGL1, and TNFRSF17. A processor generates, based on the received dataset, a score that is indicative of a predicted smoking status of the subject. The predicted smoking status may classify the subject as a current smoker or as a non-current smoker.

6 Claims, 5 Drawing Sheets

(56) References Cited

OTHER PUBLICATIONS

Rotunno et al., "A Gene Expression Signature from Peripheral Whole Blood for Stage I Lung Adenocarcinoma", Cancer Prevention Research, American Association for Cancer Reseach, vol. 4, Issue 10, Oct. 2011, pp. 1599-1608.

Showe et al., "Gene Expression Profiles in Peripheral Blood Mononuclear Cells Can Distinguish Patients with Non-Small Cell Lung Cancer from Patients with Nonmalignant Lung Disease", Cell, Tumor, and Stem Cell Biology, Cancer Research, The American Association for Cancer Research, vol. 69, Issue 24, Dec. 15, 2009, pp. 9202-9211.

* cited by examiner

200

202 RECEIVE A DATASET ASSOCIATED WITH A SAMPLE, THE DATA SET COMPRISING QUANTITATIVE EXPRESSION DATA FOR LRRN3, CDKN1C, PALLD, SASH1, RGL1, AND TNFRSF17

204 GENERATE A SCORE BASED ON THE RECEIVED DATASET, THE SCORE BEING INDICATIVE OF A PREDICTED SMOKING STATUS OF A SUBJECT

SYSTEMS AND METHODS FOR PREDICTING A SMOKING STATUS OF AN INDIVIDUAL

REFERENCE TO RELATED APPLICATIONS

This application is a U.S. Nationalization of PCT Application Number PCT/EP2014/077473 filed Dec. 11, 2014, which claims priority under 35 U.S.C. § 119 to U.S. Provisional Patent Application 61/916,443, entitled "Systems and Methods for Predicting a Smoking Status of an Individual," filed Dec. 16, 2013, each of which is incorporated herein in its entirety.

BACKGROUND

Whole genome microarrays are used as a practical means of measuring whole genome expression levels and gaining biological insights into various conditions. This approach is also used to assess the body's response to exposure to active substances and to predict the resulting phenotypes. The molecular changes in the transcriptome of a smoker's large airway cells in response to smoke exposure can be detected even when no histological abnormalities are visible. This observation indicates that transcriptome data can potentially be used for assessing the responses of biological systems to exposure of various substances.

In many product risk assessment studies, acquiring samples from a desired primary site (such as an airway) is invasive and is not convenient. As an alternative, peripheral blood sampling is minimally invasive and widely used in the general population. Therefore, there is an interest in finding and establishing biomarkers that can be reliably used in peripheral blood which acts as a surrogate tissue.

Previous attempts to discover molecular biomarkers focused on the identification of differentially expressed genes between case and control populations. Recent methods endeavor to be increasingly predictive of new cases, thereby leading to enhanced diagnosis, improved prognostic, and the advancement of personalized medicine. However, the development of computational methodologies that are robust and versatile for clinical applications remains challenging. For smoking-related diseases, diagnostic signatures in peripheral blood samples have been identified. At least two studies have shown that differentially expressed genes can discriminate subjects with early stage non-small cell lung cancer from control subjects or subjects with non-malignant lung disease (Rotunno, M., Hu, N., Su, H., Wang, C., Goldstein, A. M., Bergen, A. W., Consonni, D., Pesatori, A. C., Bertazzi, P. A., Wacholder, S., et al. (2011). A gene expression signature from peripheral whole blood for stage I lung adenocarcinoma. Cancer Prev Res (Phila) 4, 1599-1608; Showe, M. K., Vachani, A., Kossenkov, A. V., Yousef, M., Nichols, C., Nikonova, E. V., Chang, C., Kucharczuk, J., Tran, B., Wakeam, E., et al. (2009). Gene expression profiles in peripheral blood mononuclear cells can distinguish patients with non-small cell lung cancer from patients with nonmalignant lung disease. Cancer Res 69, 9202-9210).

SUMMARY

Computational systems and methods are provided for identifying a robust blood-based gene signature that can be used to predict a smoker status of an individual. The gene signature described herein is capable of accurately predicting a smoker status of an individual by being able to distinguish between subjects who currently smoke from those who have never smoked or who have quit smoking.

In certain aspects, the systems and methods of the present disclosure provide a computerized method for assessing a sample obtained from a subject. The computerized method includes receiving, by receiving circuitry, a dataset associated with the sample, the dataset comprising quantitative expression data for LRRN3, CDKN1C, PALLD, SASH1, RGL1, and TNFRSF17. A processor generates, based on the received dataset, a score that is indicative of a predicted smoking status of the subject. The predicted smoking status may classify the subject as a current smoker or as a non-current smoker.

In certain implementations, the dataset further comprises quantitative expression data for IGJ, RRM2, SERPING1, FUCA1, and ID3. In certain implementations, the score is a result of a classification scheme applied to the dataset, wherein the classification scheme is determined based on the quantitative expression data in the dataset.

In certain implementations, the method further comprises computing a fold-change value for each of LRRN3, CDKN1C, PALLD, SASH1, RGL1, and TNFRSF17, and determining that each fold-change value satisfies at least one criterion. The criterion may require that each respective computed fold-change value exceeds a predetermined threshold for at least two independent population datasets.

In certain aspects, the systems and methods of the present disclosure provide a computerized method for assessing a sample obtained from a subject. A device includes means for detecting the expression level of the genes in a gene signature comprising LRRN3, CDKN1C, PALLD, SASH1, RGL1, and TNFRSF17 in a test sample. The device also includes means for correlating the expression level with a classification of a smoker status, and means for outputting the classification of the smoker status as a prediction of the smoker status of the subject.

In certain aspects, the systems and methods of the present disclosure provide a kit for predicting smoker status of an individual. The kit includes a set of reagents that detects expression levels of the genes in a gene signature comprising LRRN3, CDKN1C, PALLD, SASH1, RGL1, and TNFRSF17 in a test sample, and instructions for using said kit for predicting smoker status in the individual.

In certain aspects, the systems and methods of the present disclosure provide a kit for assessing an effect of an alternative to a smoking product on an individual. The kit includes a set of reagents that detects expression levels of the genes in a gene signature comprising LRRN3, CDKN1C, PALLD, SASH1, RGL1, and TNFRSF17 in a test sample, and instructions for using said kit for assessing the effect of the alternative on the individual. The alternative to a smoking product may be a heated tobacco product (HTP), and the effect of the alternative on the individual may be to classify the individual as a non-smoker.

In certain aspects, the systems and methods of the present disclosure provide a method for assessing a sample obtained from a subject. The method includes receiving, by receiving circuitry, a dataset associated with the sample. The dataset comprises quantitative expression data for at least five markers selected from the group consisting of: LRRN3, CDKN1C, PALLD, SASH1, RGL1, TNFRSF17, IGJ, RRM2, SERPING1, FUCA1, and ID3. The method further includes generating, by a processor based on the received dataset, a score that is indicative of a predicted smoking status of the subject. The predicted smoking status of the subject may classify the subject as a current smoker or as a non-current smoker.

The score may be a result of a classification scheme applied to the dataset, where the classification scheme is determined based on the quantitative expression data in the dataset. The method may further include computing a fold-change value for each of LRRN3, CDKN1C, PALLD, SASH1, RGL1, and TNFRSF17, and determining that each fold-change value satisfies at least one criterion. The criterion may require that each respective computed fold-change value exceeds a predetermined threshold for at least two independent population datasets.

In certain aspects, the systems and methods of the present disclosure provide a device for assessing a sample obtained from a subject. The device includes means for detecting the expression level of the genes in a gene signature comprising at least five markers selected from the group consisting of: LRRN3, CDKN1C, PALLD, SASH1, RGL1, TNFRSF17, IGJ, RRM2, SERPING1, FUCA1, and ID3 in a test sample. The device further includes means for correlating the expression level with a classification of a smoker status, and means for outputting the classification of the smoker status as a prediction of the smoker status of the subject.

In certain aspects, the systems and methods of the present disclosure provide a kit for predicting smoker status of an individual. The kit includes a set of reagents that detects expression levels of the genes in a gene signature comprising at least five markers selected from the group consisting of: LRRN3, CDKN1C, PALLD, SASH1, RGL1, TNFRSF17, IGJ, RRM2, SERPING1, FUCA1, and ID3 in a test sample, and instructions for using said kit for predicting smoker status in the individual.

In certain aspects, the systems and methods of the present disclosure provide a kit for assessing an effect of an alternative to a smoking product on an individual. The kit includes a set of reagents that detects expression levels of the genes in a gene signature comprising at least five markers selected from the group consisting of: LRRN3, CDKN1C, PALLD, SASH1, RGL1, TNFRSF17, IGJ, RRM2, SERPING1, FUCA1, and ID3 in a test sample, and instructions for using said kit for assessing the effect of the alternative on the individual. The alternative to the smoking product may be an HTP, and the effect of the alternative on the individual may be to classify the individual as a non-smoker.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which.

DETAILED DESCRIPTION

Figure 1:
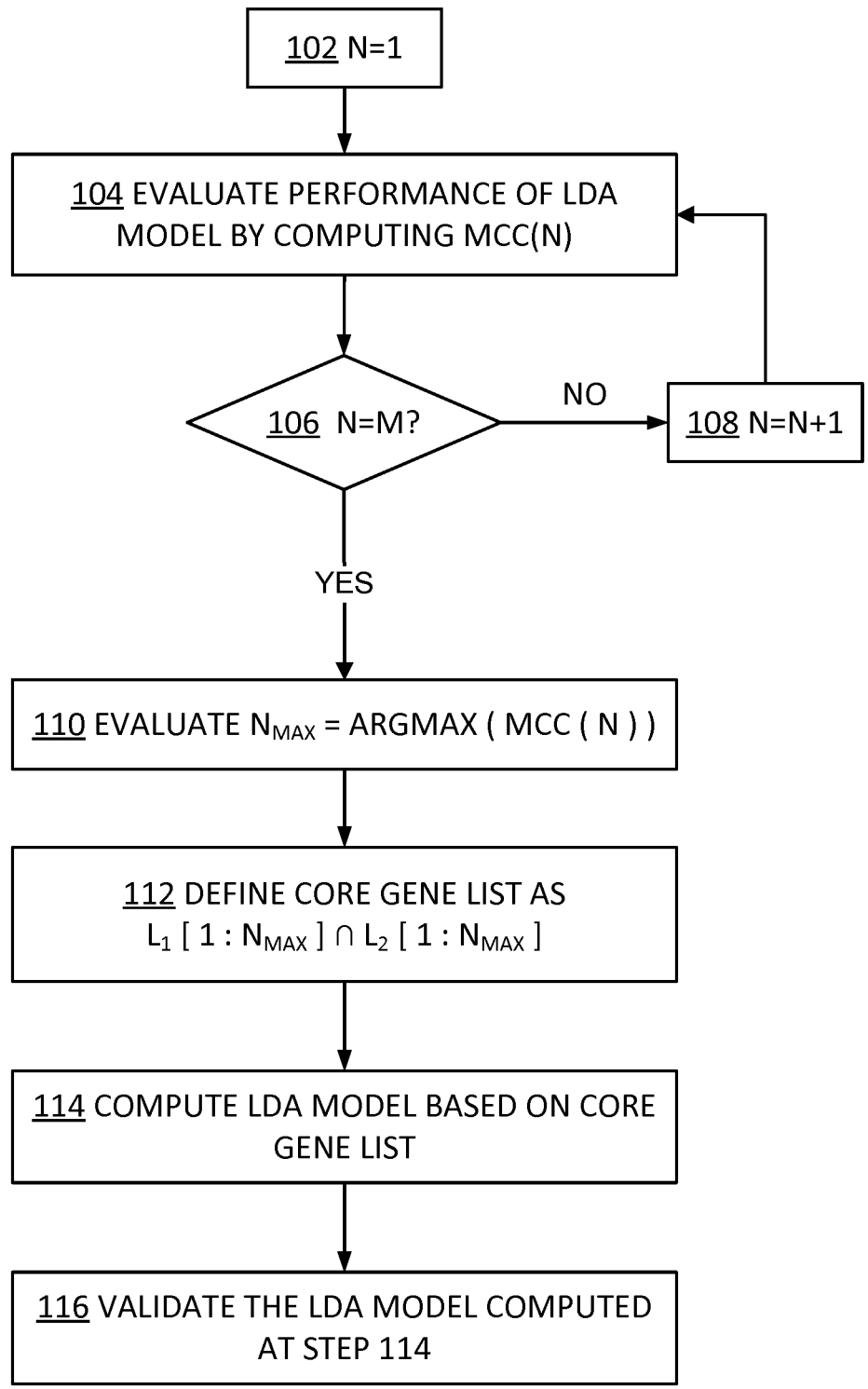
FIG. 1 is a flowchart of a process for identifying a set of genes and obtaining a classification model based on the set of genes.

Described herein are computational systems and methods for identifying a robust blood-based gene signature that can be used to predict a smoker status of an individual. In particular, the gene signature described herein is capable of distinguishing between subjects who currently smoke from those who have never smoked or who have quit smoking.

As used herein, a "robust" gene signature is one that maintains a strong performance across studies, laboratories, sample origins, and other demographic factors Importantly, a robust signature should be detectable even in a set of population data that includes large individual variations. Robustness across datasets should also be properly validated in order to avoid over-optimistic reporting of the signature's performance.

One goal of the present disclosure is to obtain a gene signature that can accurately predict a smoker status of an individual. To evaluate the performance of a gene signature, the prediction results are shown herein in tables that display a predicted status in the rows and a true status in the columns. Table 1 shown below is an example of one way to display the prediction results. The first row of the table indicates the number of true current smokers and non-current smokers whose samples were predicted to be associated with a current smoker, and the second row of the table indicates the number of true current smokers and non-current smokers whose samples were predicted to be associated with a non-current smoker.

TABLE 1

|  | Current Smoker | Non-current Smoker |
| --- | --- | --- |
| Predicted Current Smoker | True Positives | False Positives |
| Predicted Non-current Smoker | False Negatives | True Negatives |

A perfect predictor will have all of the current smokers accurately predicted as current smokers (true positives will be 100% and false negatives will be 0%), and all non-current smokers will be accurately predicted as non-current smokers (true negatives will be 100% and false positives will be 0%). As described herein, individuals are classified according to a smoking status (e.g., current smoker, non-current smoker, former smoker, never smoker, etc.), but in general, one of ordinary skill in the art will understand that the systems and methods described herein are applicable to any classification scheme.

To evaluate the strength of a predictor, various metrics based on the values in the prediction results table may be used. One metric is referred to herein as "sensitivity," which is the proportion of individuals who were accurately classified as current smokers out of the set of current smokers. In other words, the sensitivity metric is equal to the number of true positives, divided by the sum of the true positives and the false negatives, or TP/(TP+FN). A sensitivity value of one indicates perfect classification for the current smokers. Another metric is referred to herein as "specificity," which is the proportion of individuals who were accurately classified as non-current smokers out of the set of non-current smokers. In other words, the specificity metric is equal to the number of true negatives, divided by the sum of the true negatives and the false positives, or TN/(TN+FP). A specificity value of one indicates perfect classification for the non-current smokers. To be considered a strong predictor, high values in both sensitivity and specificity are desirable. While sensitivity and specificity metrics are used herein for evaluating the performance of the predictors, in general, any other metrics may also be used without departing from the scope of the present disclosure, such as the predictive value of a positive test (TP/(TP+FP)) or the predictive value of a negative test (TN/(TN+FN)).

The systems and methods described herein build a prediction model by first identifying genes that exhibit high fold-change in their expression levels from different training datasets. Then, the identified set of genes was validated with an independent dataset. After validation, the gene set was tested by evaluating the blood transcriptome of subjects with known smoker statuses and comparing the expression levels from the identified set of genes for individuals with one smoker status to individuals with another smoker status. The resulting set of genes that is successfully validated and tested is referred to herein as a "gene signature."

The gene signature can be used to accurately classify individuals into specific predicted smoker status groups. Moreover, by being able to accurately predict a smoker status of an individual, the gene signature is able to detect the use of various HTPs by comparing the results of individuals who use an HTP and individuals who smoke conventional cigarettes. The gene signature may be used in a situation where compliance regarding smoking behavior is required. In an example, the predicted smoker status of an individual (as determined by the gene signature) may be used in a clinical trial for an HTP to identify whether or when biological changes to the individual occur after the individual switches to an HTP. In general, the gene signature may be used in any health-related study that monitors cigarette smoking, smoking cessation, or switching to an HTP.

In one example, data from several publicly available gene expression datasets that profiled blood samples from current smokers and non-smokers or former smokers were obtained. Pre-selecting genes based on high fold-change genes from various independent studies is advantageous as doing so enhances the robustness of the signature across different studies and ensures that the prediction model is not biased by a single dataset. Validation is performed with an independent dataset derived from a clinical study that aimed to discover novel biomarkers for COPD. In addition, from another clinical study, the blood transcriptome of smokers who switched from conventional cigarettes (which combusts tobacco) to an HTP (that does not combust tobacco; herein referred to Tobacco Heating System (THS) 2.1) for 5 consecutive days was evaluated and compared with those who continued to smoke conventional cigarettes. The signature described herein performed remarkably well in classifying current smokers and non-current smokers as demonstrated by its performance using independent datasets. In addition, the impact of switching to THS 2.1 for 5 days was detectable in the blood transcriptome as subjects who switched to THS 2.1 were classified as non-current smokers. This suggests that the gene signatures and the systems and methods herein may be useful not only for determining the smoker status but also in evaluating the short-term effects of cigarette smoking.

Using a signature that is based on a limited number of genes is advantageous relative to using the whole transcriptome for reducing costs and workload because the analyses will eventually be based on quantitative reverse transcriptase-polymerase chain reaction (qRT-PCR) measurements. The investment in equipment and running cost, such as reagents, for using qRT-PCR is more favorable than using microarrays.

In an example, different training datasets are obtained in a first step to identify a gene signature. Specifically, two training datasets were used herein: BLD-SMK-01 and QASMC. However, in general, any number of any combination of training datasets may be used without departing from the scope of the disclosure.

Blood samples collected using the PAXgene blood DNA kit (Qiagen) for BLD-SMK-01 were obtained from a banked repository (BioServe Biotechnologies Ltd, Beltsville, Md. 20705 USA). At the time of sampling, the ages of the subjects were between 23 and 65 years. Subjects with no disease history and subjects that were taking prescription medications were excluded. Current smokers had smoked at least 10 cigarettes per day for at least 3 years. Former smokers had ceased smoking at least 2 years prior to sampling and before quitting had smoked at least 10 cigarettes per day for at least 3 years. Current smokers and non-smokers were matched by age and gender. A total of 31 blood samples were obtained from current smokers, 30 from never smokers, and 30 from former smokers.

Blood samples were also obtained from the Queen Ann Street Medical Center (QASMC) clinical study, which was conducted at The Heart and Lung Centre in London, UK, according to Good Clinical Practice (GCP) and was registered on ClinicalTrials.gov with the identifier, NCT01780298. The QASMC study aimed to identify biomarker or a panel of biomarkers that would enable the differentiation between subjects with COPD (current smokers with a ≥10 pack year smoking history at GOLD Stage 1 or 2) and three control groups of matched non-smoking subjects: never smokers, former smokers and current smokers. Samples from sixty subjects in each of the four groups were obtained (240 subjects in total). Male and female subjects aged between 40 and 70 years were included. All subjects were matched by ethnicity, gender and age (within 5 years) with the COPD subjects recruited in the study. Blood samples were sent to AROS Applied Biotechnology AS (Aarhus, Denmark) where they were further processed and then hybridized to Affymetrix Human Genome U133 Plus 2.0 GeneChips, as described below.

Total RNAs (including microRNAs) were isolated using the PAXgene Blood miRNA Kit (catalog number, 763134; Qiagen) according to the manufacturer's instructions. The concentration and purity of the RNA samples were determined using a UV spectrophotometer (NanoDrop ND1000; Thermo Fisher Scientific, Waltham, Mass., USA) by measuring the absorbance at 230, 260 and 280 nm. The integrity of the RNA was further checked using an Agilent 2100 Bioanalyzer. Only RNAs with an RNA integrity number (RIN) of above 6 were processed for further analysis.

RNA Preparation and Affymetrix Hybridization.

Affymetrix probe sets targeting the 3' ends of transcripts were prepared from 50 ng of RNA using the NuGEN™ Ovation™ Whole Blood Reagent and NuGEN™ Ovation™ RNA Amplification System V2. The quantity of cDNA was e measured with a Nanodrop 1000 or 8000 spectrophotometer (Thermo Fisher Scientific) or a SpectraMax 384Plus (Molecular Devices). The quality of the cDNA was determined by assessing the size of the un-fragmented cDNA using an Agilent 2100 Bioanalyzer. The size distribution of the final fragmented and biotinylated product was also monitored using electropherograms. After labeling the cDNA, the fragments were hybridized to the GeneChip Human Genome U133 Plus 2.0 Array according to the manufacturer's guidelines. Samples for target preparation were fully randomized for the Affymetrix gene expression microarray.

Taqman qRT-PCR Assay.

Reverse transcription reactions were performed using the iScript™ cDNA Synthesis Kit (catalog number, 170-8890;

Bio-Rad, Hercules Calif., USA) with 500 ng of starting RNA according to the manufacturer's instructions. Then, the cDNAs were diluted to exactly 10 ng/μL. A commercial human universal RNA (UHR) reference (Cat#740000, Agilent Technologies, Santa Clara, Calif., USA) was added to the sample as a calibrator to reliably compare the data across multiple experiments and instruments. The probes used in the Taqman assays spanned exons, and five housekeeping genes (B2M, GAPDH, FARP1, A4GALT, GINS2) were chosen for the data normalization step. The qPCR step was carried out using Taqman® assays and TaqMan® Fast Advanced Master Mix (cat: 444963). Briefly, cDNAs were diluted to allow the application of 1.25 ng per well in a 384-well plate. In parallel, a master mix (of Taqman assay reagents and Taqman Advanced Mix) was prepared for each Taqman assay. The final reaction volume was 10 μL. The qPCR was run using a Viia7 instrument (Life Technologies) and the automatic baseline and default $C_t$ threshold settings were applied for analyzing the results. As an Universal Human Reference (UHR) sample was added, the $C_t$ values were normalized for each gene (by subtraction) with respect to the UHR $C_t$ values and then to the GAPDH housekeeping gene values (leading to the so-called $\Delta\Delta C_t$ value).

Taqman primers were obtained from Life Technologies, CA, USA. Below, Table 2 lists the primer sequences used for performing the qRT-PCR.

Microarray Analysis—Data Quality Check and Normalization.

After investigation of the chip images to detect artifacts on the chip scan, the data were processed through standard quality control pipeline. Briefly, raw data files were read using the ReadAffy function of the affy package (Gautier, L., Cope, L., Bolstad, B. M., and Irizarry, R. A. (2004). affy—analysis of Affymetrix GeneChip data at the probe level. Bioinformatics 20, 307-315) from the Bioconductor suite of microarray analysis tools (Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol 5, R80) available for the R statistical environment (R Development Core Team (2007). R: A Language and Environment for Statistical Computing). Quality was controlled by generating and examining RNA degradation plots (AffyRNAdeg function of the affy package), [09:42:29] Normalized Unsealed Standard Error plots, Relative Log Expression plots (affyPLM package (Brettschneider, J., Collins, F., and Bolstad, B. M. (2008). Quality Assessment for Short Oligonucleotide Microarray Data. Technometrics 50, 241-264)), and the Mean Average of Relative Log Expression values. Additionally, an eye-check of the pseudo-images (residuals of the probe-level models) was done to ensure that no spatial effect was

TABLE 2

| Assay ID | Availability | Catalog Number | Assay Type | Gene Symbol | Gene Name |
| --- | --- | --- | --- | --- | --- |
| Hs00539582_s1 | Inventoried | 4331182 | GE | LRRN3 | hCG1643830 Celera Annotation; leucine rich repeat neuronal 3 |
| Hs03045080_m1 | Inventoried | 4331182 | GE | TNFRSF17 | hCG14623 Celera Annotation; tumor necrosis factor receptor superfamily; member 17 |
| Hs00376160_m1 | Inventoried | 4331182 | GE | IGJ | hCG17003 Celera Annotation; immunoglobulin J polypeptide; linker protein for immunoglobulin alpha and mu polypeptides |
| Hs00323932_m1 | Inventoried | 4331182 | GE | SASH1 | hCG16768 Celera Annotation; SAM and SH3 domain containing 1 |
| Hs00357247_g1 | Inventoried | 4331182 | GE | RRM2 | hCG23833 Celera Annotation; ribonucleotide reductase M2 |
| Hs00363100_m1 | Inventoried | 4331182 | GE | PALLD | palladin; cytoskeletal associated protein; hCG2026123 Celera Annotation |
| Hs00954037_g1 | Inventoried | 4331182 | GE | ID3 | hCG1982882 Celera Annotation; inhibitor of DNA binding 3; dominant negative helix-loop-helix protein |
| Hs00163781_m1 | Inventoried | 4331182 | GE | SERPING1 | serpin peptidase inhibitor; clade G (C1 inhibitor); member 1; hCG39766 Celera Annotation |
| Hs00175938_m1 | Inventoried | 4331182 | GE | CDKN1C | cyclin-dependent kinase inhibitor 1C (p57; Kip2); hCG1782992 Celera Annotation |
| Hs00609173_m1 | Inventoried | 4331182 | GE | FUCA1 | hCG1739246 Celera Annotation; fucosidase; alpha-L-1; tissue |
| Hs99999907_m1 | Inventoried | 4331182 | GE | B2M | hCG1786707 Celera Annotation; beta-2-microglobulin |
| Hs02758991_g1 | Inventoried | 4331182 | GE | GAPDH | glyceraldehyde-3-phosphate dehydrogenase; hCG2005673 Celera Annotation |
| Hs00195010_m1 | Inventoried | 4331182 | GE | FARP1 | hCG1811328 Celera Annotation; FERM; RhoGEF (ARHGEF) and pleckstrin domain protein 1 (chondrocyte-derived) |
| Hs00213726_m1 | Inventoried | 4331182 | GE | A4GALT | alpha 1; 4-galactosyltransferase; hCG1640515 Celera Annotation |
| Hs00211479_m1 | Inventoried | 4331182 | GE | GINS2 | GINS complex subunit 2 (Psf2 homolog); hCG15657 Celera Annotation |
| Hs00248508_m1 | Inventoried | 4331182 | GE | RGL1 | hCG2025089 Celera Annotation; ral guanine nucleotide dissociation stimulator-like 1 | present. Arrays that fell below a set of thresholds on the quality control checks were excluded from further analysis.

For the population-level analysis (i.e., study of the average fold-changes), the data were subsequently normalized using GC-Robust Microarray Analysis (GC-RMA). Background correction and quantile normalization were used to generate microarray expression values (Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264) from all arrays passing quality control checks. For the individual signature prediction model, the data were normalized with MASS (Affymetrix, I. (2002). Statistical algorithms description document. Technical paper).

Statistical Modeling—Population Level Analysis.

For each comparison, an overall linear model was fit to generate raw p-values for each probe set on the expression array based on moderated t-statistics. The Benjamini-Hochberg False Discovery Rate (FDR) method was used to correct for multiple testing effects that arise as large numbers of genes are evaluated.

Statistical modeling—Individual sample prediction modeling. To achieve robustness in the prediction model, independent gene expression datasets from blood (GSE15289) and PBMCs (GSE42057) were obtained from the National Center for Biotechnology Information Gene Expression Omnibus (GEO) (http://www.ncbi.nlm.nih.gov/gds/?term=GEO) and processed. The dataset from the NOWAC study (GSE15289) (Dumeaux, V., Olsen, K. S., Nuel, G., Paulssen, R. H., Borresen-Dale, A.-L., and Lund, E. (2010a). Deciphering normal blood gene expression variation—The NOWAC postgenome study. PLoS genetics 6, e1000873) included whole blood samples from 285 post-menopausal women aged between 48 and 63 years old, including 211 never smokers and 74 current smokers. The dataset of Bahr et al. (GSE42057) (Bahr, T. M., Hughes, G. J., Armstrong, M., Reisdorph, R., Coldren, C. D., Edwards, M. G., Schnell, C., Kedl, R., LaFlamme, D. J., and Reisdorph, N. (2013). Peripheral Blood Mononuclear Cell Gene Expression in Chronic Obstructive Pulmonary Disease. American journal of respiratory cell and molecular biology) was derived from peripheral blood mononucleated cell (PBMC) samples collected from 36 current smokers (of which 22 have COPD and 14 are healthy) and 100 former smokers (of which 72 have COPD and 28 are healthy). All subjects were non-Hispanic white.

Data sampled from the subjects in the GSE15289 and GSE42057 datasets were used to identify genes that exhibited high changes in average expression between samples from smokers and never (or former) smokers in each datasets. Let $L_1$ and $L_2$ be the set of the M (here, M=1000 but in general, M can be any value) highest fold-change genes from the two independent datasets (GSE15289 and GSE42057). To obtain the list $L_1$, the dataset GSE15289 was sorted according to smoker status (current smoker and never smoker), and the average gene expression levels were obtained for each group. The difference in the average gene expression levels between the current smoker group and the never smoker group are referred to herein as the fold-changes, and the M genes with the highest fold-changes are included in the set $L_1$. The list $L_2$ was similarly obtained, but for current smokers and former smokers.

FIG. 1 is a flowchart of a process 100 for identifying a set of genes and obtaining a classification model based on the set of genes. In particular, the process 100 includes the steps of initializing a counter parameter N to 1 (step 102), evaluating the performance of a linear discriminant analysis (LDA) model by computing a Matthews Correlation Coefficient (MCC(N)) (step 104), and determining whether the counter parameter is equal to a maximum counter value M (decision block 106). If N is less than M, process 100 proceeds to step 108 to increment N and returns to step 104 to evaluate the performance of an LDA model by computing the next coefficient MCC(N). When N reaches M (decision block 106), the value of N ($N_{MAX}$) that results in the maximum MCC value is evaluated (step 110), and the core gene list is defined as an intersection between the two gene sets $L_1[1:N]$ and $L_2[1:N]$ (step 112). After the core gene list is identified, the LDA model is computed based on the core gene list (step 114).

At step 102, the counter parameter N is initialized to 1. The counter parameter N varies from 1 to a maximum value M and is incremented at step 108 until N reaches M at decision block 106.

At step 104, the performance of an LDA model is evaluated by computing the coefficient MCC(N). In particular, the performance of an LDA model may be evaluated using 5-fold cross-validation (100 times) on $L_1[1:N] \cap L_2[1:N]$, which is the intersection of the N highest fold-changes in the set $L_1$ and the N highest fold-changes in the set $L_2$. The LDA model is evaluated by computing the MCC(N). The MCC metric combines all the true/false positive and negative rates, and thus provides a single valued fair metric. The MCC is a performance metric that may be used as a composite performance score. The MCC is a value between −1 and +1 and is essentially a correlation coefficient between the known and predicted binary classifications. The MCC may be computed using the following equation:

$$MCC = \frac{TP*TN - FP*FN}{\sqrt{(TP+FP)*(TP+FN)*(TN+FP)*(TN+FN)}}$$

where TP: true positive; FP: false positive; TN: true negative; FN: false negative. However, in general, any suitable technique for generating a composite performance metric based on a set of performance metrics may be used to assess the performance of the LDA model. An MCC value of +1 indicates that the model obtains perfect prediction, an MCC value of 0 indicates the model predictions perform no better than random, and an MCC value of −1 indicates the model predictions are perfectly inaccurate. MCC has an advantage of being able to be easily computed when the classifier function is coded in a way that only class predictions are available. In contrast, for an area under the curve (AUC) computation, the classifier function is required to provide a numerical score. However, in general, any metric that accounts for TP, FP, TN, and FN may be used in accordance with the present disclosure.

Figure 4:
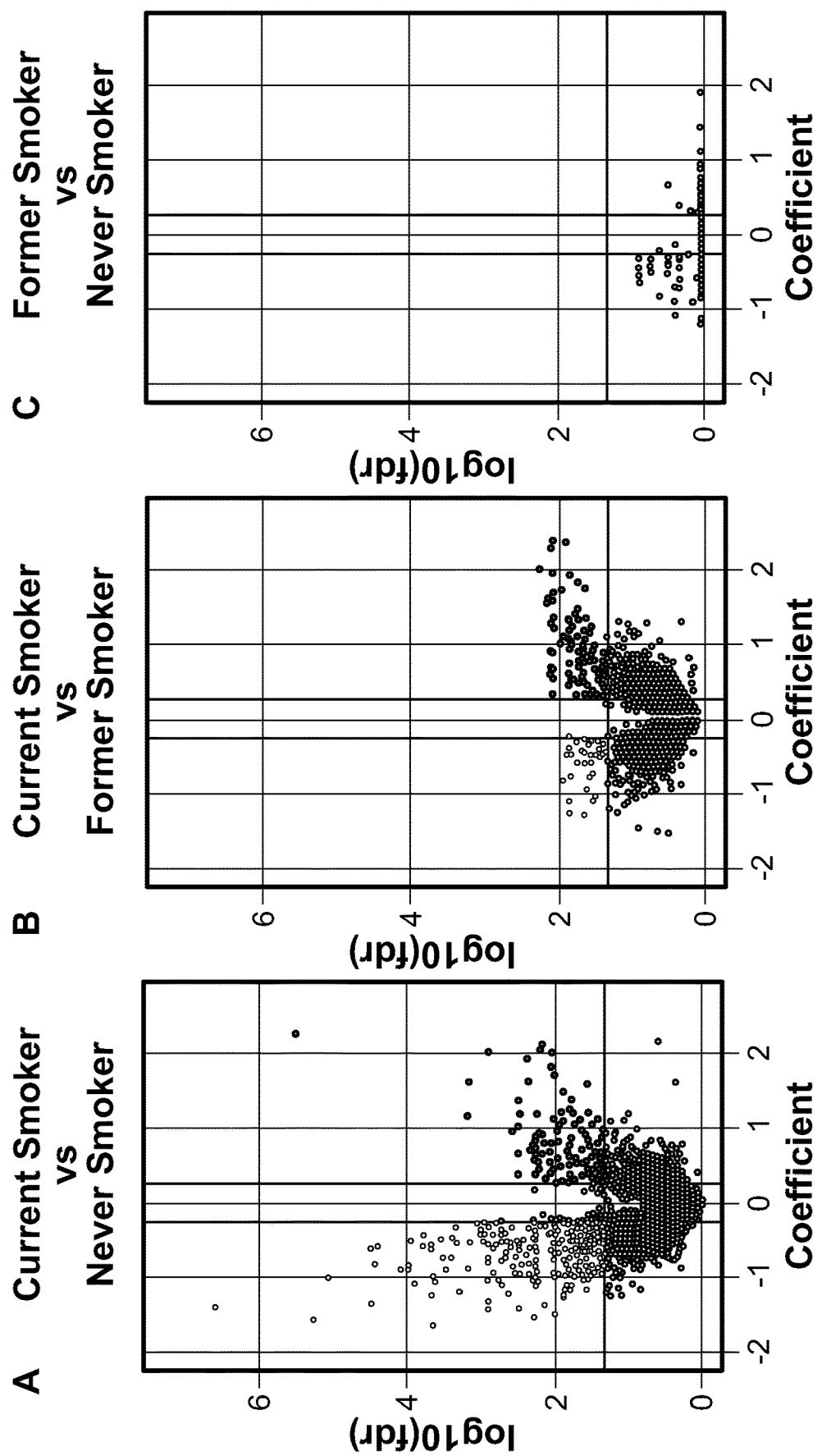
FIGS. 4A, 4B, and 4C are volcano plots for differentially expressed genes in a dataset of samples.

To compute the MCC, the set of classification categories should first be selected. The BLD-SMK-01 dataset was taken from never smokers, former smokers, and current smokers. FIGS. 4A, 4B, and 4C show volcano plots for the differentially expressed genes in BLK-SMK-01 samples. Each volcano plot shows the estimated log 2 (fold-change) against −log 10 (adjusted P-value). The P-values were computed based on moderated t-statistics and were adjusted by the Benjamini Hochberg method. Specifically, FIG. 4A compares the gene expression profiles between current smokers and non-smokers, FIG. 4B compares the gene expression profiles between current smokers and former smokers, and FIG. 4C compares the gene expression profiles between former smokers and never-smokers. The volcano plots shown in FIG. 4C indicates no differential gene expression changes between never smokers and former smokers (i.e., no trend is observed in FIG. 4C), but FIGS. 4A and 4B indicate that many differential gene expression changes are observed between current smokers and never smokers (FIG. 4A) and between current smokers and former smokers (FIG. 4B).

Thus, the population level transcriptomic analysis of BLD-SMK-01 samples indicates that there are no differential gene expression changes between never smokers and former smokers in whole blood, and hence distinguishing between former and never smokers based on the blood transcriptome would be very challenging. Conversely, there are many differentially expressed genes between current smokers and never smokers and former smokers, respectively (FIGS. 4A and 4B). Because no difference was observed between the population of the never smokers and the former smokers, only two categories were used to evaluate the model at step 104: current smokers and non-current smokers.

Specifically, at step 104, the set of genes $L_1[1:N] \cap L_2[1:N]$ corresponds to the intersection of the N highest fold-changes from the two independent datasets GSE15289 and GSE42057. Each prediction model based on either $L_1[1:N]$, $L_2[1:N]$ is cross-validated to assess whether the results of the LDA model are generalizable to an independent dataset. In an example, to perform one instance of a 5-fold cross-validation on the $L_1[1:N]$ set of genes, the $L_1[1:N]$ set was randomly divided into five subsets: A, B, C, D, and E. Four (A, B, C, and D) subsets were used to train a classifier using an LDA technique, and a fifth subset (E) was used to test the classifier that was trained on the other four subsets. This training and testing process was repeated four more times, with each of the other subsets (A, B, C, and D) being used as the testing subset for testing a classifier that was trained on the other four subsets.

In general, the criterion of an LDA technique is to classify an input vector x describing n features into a class y. The classification is based on a function that is a linear combination of the observed features. The coefficients of the linear combination are estimated based on the training subsets of data. Specifically, to train a classifier using the LDA technique, a linear combination of the gene expression levels in the data from the four training subsets is identified. The linear combination is referred to herein as a classifier and defines a border between a predicted smoker status and a predicted non-smoker status. The classifier is used to obtain a predicted status for each individual in the testing subset. This process is repeated four more times, such that each of the five subsets has been processed as the testing subset once. After each of the five subsets has been the testing subset one time, one instance of the 5-fold cross-validation is complete, and the training data observations (with features in the $L_1[1:N] \cap L_2[1:N]$ set) are divided into five new subsets A', B', C', D', and E' to initiate a second instance of the 5-fold cross-validation.

The examples described herein are results of 100 instances of the 5-fold cross-validation, but in general, one of ordinary skill in the art will understand that any number of instances of k-fold cross-validation may be used without departing from the scope of the present disclosure. Moreover, the examples described herein are results of an LDA technique, which forms a classifier based on a linear combination of the gene expression levels. However, in general, one of ordinary skill in the art will understand that any function of the gene expression levels may be used to form a classifier, such as quadratic functions, polynomial functions, exponential functions, or any other suitable functions that may form a 1-dimensional manifold in R^N to define a classifier.

At step 110, after N reaches the maximum number M, the set of M values of MCC are considered, and the value of N corresponding to the maximum value of MCC is evaluated as $N_{max} = \text{argmax}_N(MCC(N))$. As shown in FIG. 1, the step of evaluating $N_{max}$ is performed after all M values of MCC have been computed. However, in general, one of ordinary skill in the art will understand that alternatively, the value of MCC(N) computed at step 104 may be compared to some predetermined threshold value before evaluating the next value of MCC(N+1). In this case, when a value MCC is found that exceeds the predetermined threshold, the process 100 may proceed directly to step 110 assign the value of $N_{max}$ to the current value of N, without considering the remaining values of $N=N_{max}+1$ to M.

At step 112, the core gene list for the signature is defined by the intersection $L_1[1:N_{max}] \cap L_2[1:N_{max}]$, or the set of genes that are in both $L_1[1:N_{max}]$ and $L_2[1:N_{max}]$. As described in this example, only two datasets are used $L_1$ and $L_2$. However, in general, one of ordinary skill in the art will understand that any number of datasets may be used to compute MCC values and identify a core set of genes defining a gene signature. In particular, the intersection of m datasets, or the union of pairwise intersections may be used.

At step 114, the core gene list determined at step 112 is used to compute an LDA model. In particular, the LDA model computed based on the core gene list may be computed by performing 5-fold cross-validation 100 times, or any number of n-fold cross-validation.

In one example, applying the statistical modeling methodology described in relation to steps 102 to 114, a core gene signature was identified that includes the following six genes: LRRN3, SASH1, PALLD, RGL1, TNFRSF17 and CDKN1C. The 5-fold cross-validation (100 times) MCC of this model was 0.77 (with a sensitivity score (Se) of 0.91 and a specificity score (Sp) of 0.85) when classifying samples obtained from current smokers versus never smokers. By design of the methodology, the core genes in the signature were among the high-fold change genes in both the NOWAC (GSE15289) and the Bahr et al. (GSE42057) studies and the prediction improved on the performance of an LDA model based on all 77 common genes between those two GSE-studies (Se=0.73, Sp=0.81). Even though all six genes LRRN3, SASH1, PALLD, RGL1, TNFRSF17 and CDKN1C are referred to herein as the core gene signature, one of ordinary skill in the art will understand that any combination of the six genes may be used as the core gene signature, such as any combination of three, four, or five out of the six genes.

In some embodiments, the genes in the signature were expanded to include an extended set of genes that included additional genes not in the core set that were associated with high specificity and sensitivity scores. In particular, when studying predictive models obtained by leveraging each list of high fold-change genes individually, IGJ, RRM2, ID3, SERPING1 and FUCA1 were repeatedly identified as potential candidates in signatures having a high specificity and sensitivity. These five genes were also among the high fold-change genes in the blood transcriptomes of both the NOWAC (current smokers vs. never smokers) and Bahr et al. (current smokers vs. former smokers) studies and were used to extend the core gene signature to an extended signature. The cross-validation MCC of the model based on the extended signature (LRRN3, SASH1, PALLD, RGL1, TNFRSF17, CDKN1C, IGJ, RRM2, ID3, SERPING1 and FUCA1) was 0.73 (Se=0.88, Sp=0.84) when classifying current smokers vs. never smokers. Even though all eleven genes LRRN3, SASH1, PALLD, RGL1, TNFRSF17, CDKN1C, IGJ, RRM2, ID3, SERPING1 and FUCA1 are referred to herein as the extended gene signature, one of ordinary skill in the art will understand that any combination of the eleven genes may be used as the core gene signature, such as any combination of five, six, seven, eight, nine, or ten out of the eleven genes. Moreover, the combination may include combination of three, four, or five out of the six genes in the core gene signature and two, three, or four out of the five genes in the additional genes in the extended gene signature.

The results of the LDA model computed at step 114 were compared with the prediction cross-validation results of a model obtained when learning a sparse signature from BLD-SMK-01 alone (i.e. without using the two public datasets GSE15289 and GSE42057). The 5-fold cross-validation performance of this model in predicting smokers vs. non-smokers resulted in Sp=0.96 and Se=0.93, which is slightly above the performance of models based on the core and extended signatures. Even though the cross-validation specificity and sensitivity (Sp=0.88, Se=0.84) of the prediction model derived with the methodology described herein resulted in slightly lower performance than the model obtained without using independent datasets (Sp=0.96, Se=0.93), the prediction model derived herein is advantageous because the model is associated with a wider range of applications. In particular, the prediction model derived according to the methods of the present disclosure is robust, as is demonstrated when the model is validated as is described in detail in relation to step 116.

At step 116, the LDA model computed at step 114 is validated. Validation of the LDA model was performed by using the former smoker group from the BLD-SMK-01 study and the blood dataset from the QASMC study. After quality checking the QASMC transcriptomics samples, 52 COPD, 58 current smokers, 58 former smokers and 59 never smokers CEL files were available for predictions. To evaluate the prediction performance of the core and extended signatures, the QASMC samples were stratified into two groups: current smokers (COPD and healthy) and non-current smokers comprising both former and never smokers. These groups allowed for evaluation of the robustness of the signature with respect to the COPD status. Each centered dataset was predicted using the model built on the core gene signature or the extended signature.

Table 3 shows prediction results using an LDA model on the independent datasets for the various signatures. The format of Table 3 follows the format of Table 1, with predicted classifications shown in the different rows and the actual classifications shown in the different columns. In particular, the prediction results shown in Table 3 include those for the core gene signature (first three rows), the extended gene signature (middle three rows), a signature derived from the BLD-SMK-01 samples alone (second to last row), and a signature based on a set of genes described in Beineke et al. (Beineke, P., Fitch, K., Tao, H., Elashoff, M. R., Rosenberg, S., Kraus, W. E., and Wingrove, J. A. (2012). A whole blood gene expression-based signature for smoking status. BMC medical genomics 5, 58.) (bottom row). As shown in Table 3, both the core signature and the extended signature lead to higher sensitivity and specificity scores than the signatures derived from the BLD-SMK-01 samples alone and the signature identified by Beineke.

TABLE 3

|  |  | BLD-SMK-01 | QASMC | |
|---|---|---|---|---|
|  |  | Former Smoker | Current Smoker | Non-current Smoker |
| Core | Current Smoker | 3 | 99 | 12 |
|  | Non-current Smoker | 23 | 11 | 105 |
|  | True Rate | Sp = 0.88 | Se = 0.90 | Sp = 0.90 |
| Extended | Current Smoker | 4 | 100 | 12 |
|  | Non-current Smoker | 22 | 10 | 105 |
|  | True Rate | Sp = 0.85 | Se = 0.91 | Sp = 0.90 |
| Other | BLD-SMK-01 | Sp = 0.73 | Se = 0.81 | Sp = 0.77 |
|  | Beineke | Sp = 0.73 | Se = 0.87 | Sp = 0.79 |

The classification performance of the signature against the QASMC study confirmed that the model was robust regardless of COPD status (Se=0.9, Sp=0.9 for the core signature and Se=0.91, Sp=0.90 for the extended signature)

Figure 5:
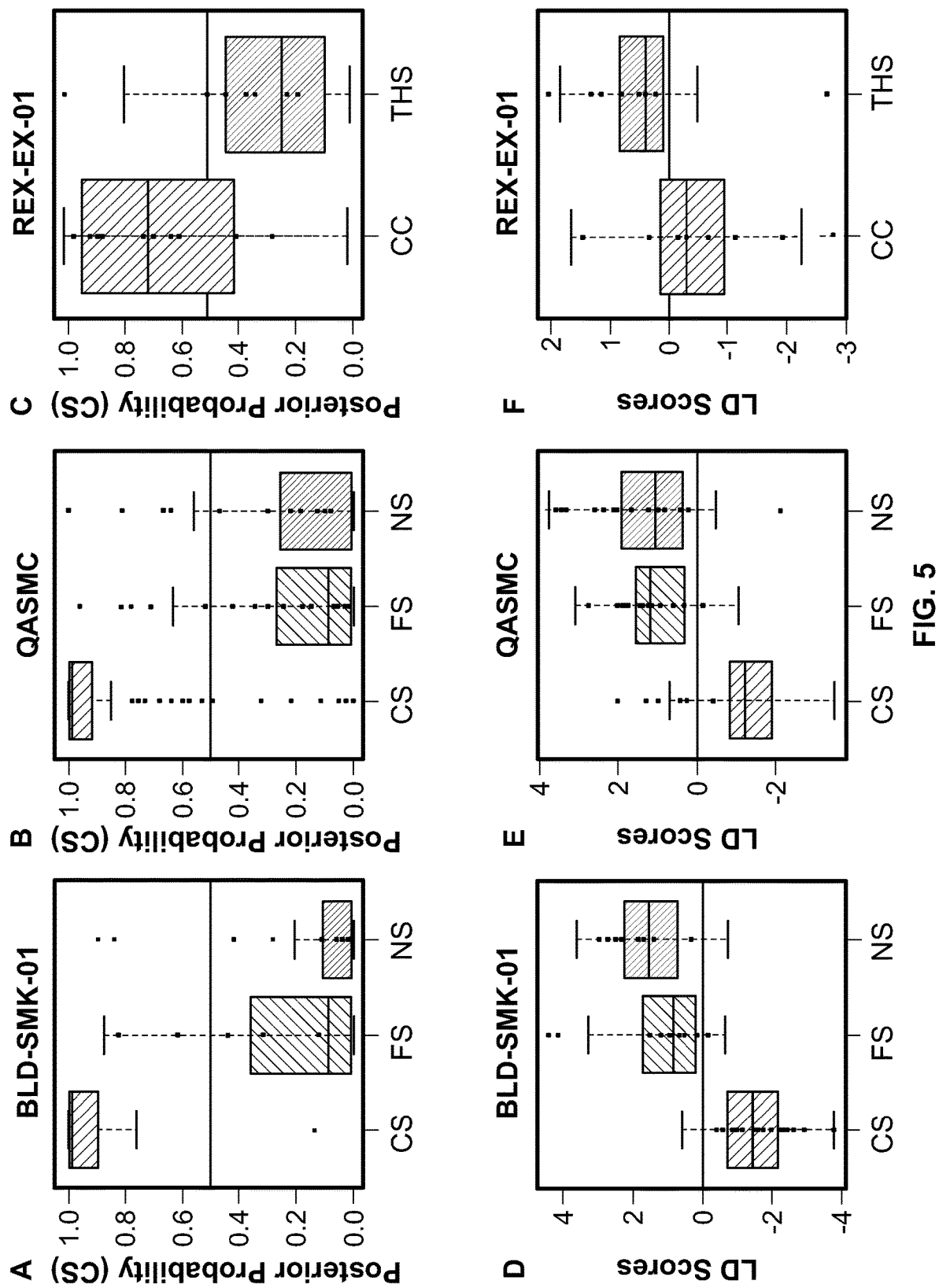
FIGS. 5A, 5B, 5C, 5D, 5E, and 5F are various boxplots indicative of classification schemes for the different studies.

Moreover, FIGS. 5A, 5B, 5D, and 5E show various boxplots indicative of classification schemes for the different studies. In particular, FIGS. 5A and 5B plot boxplots of the posterior probabilities of a sample being classified as a current smoker from the LDA model for the BLD-SMK-01 study and the QASMC study, respectively. FIGS. 5D and 5E plot boxplots of the prediction scores from the linear discriminant function for the BLD-SMK-01 study and the QASMC study, respectively. In particular, a sample with a negative score is classified as a current smoker, and a sample with a positive score is classified as a non-current smoker.

The effects of additional covariates such as gender and age were also examined. The BLD-SMK-01 and QASMC studies were balanced with respect to gender and age. No statistical association between age or gender and smoking status was present as indicated by a statistical chi-squared test ($\chi^2$(Gender, Smoking Status) P-value=1 for BLD-SMK-01 and $\chi^2$(Gender, Smoking Status) P-value=0.9 for QASMC) and a statistical t-test (t-test (Age vs. Smoking Status) P-value=0.8 for BLD-SMK-01 and t-test (Age vs. Smoking Status) P-value=0.46 for QASMC).

In addition, each gene in the signature was tested for association with gender and age in BLD-SMK-01, and the ANOVA P-values for none of the genes were below 0.05, except for the PALLD gene which showed a minor gender effect. Previously identified gene signatures found effects of gender and/or age and determined it was necessary to adjust for such factors. Beineke et al. 2012. In particular, age was an important covariate in two of the public datasets (GSE15289 and GSE42057) as smokers were on average older than never or former smokers, this covariate was not included in the predictor as it had no statistical association with smoking status in BLD-SMK-01 study. However, in addition to better performance as defined by the specificity and sensitivity scores, the gene signatures described herein are generally not correlated with gender or age. This suggests that the core signature and extended signature described herein offers an advantage over known gene signatures in that adjustment for these factors is unnecessary, thereby simplifying the computational processes.

To determine whether the discovered signature could be translated into a qRT-PCR-based exposure biomarker, a subset of twenty randomly selected samples (ten current smokers and ten never smokers) was subjected to qRT-PCR to measure the expression levels of the genes in the extended signature. An LDA model was trained on the normalized qRT-PCR data based on the genes in the extended signature and assessed by 10-fold cross-validation (1000 times, 10-fold was chosen because of the small sample size), leading to a specificity of 0.85 and sensitivity of 0.96 (Table 4). When applying the same to the core signature, a specificity of 0.62 and a lower sensitivity of 0.80 are obtained (Table 4).

TABLE 4

|  |  | Current Smoker | Non-current Smoker |
|---|---|---|---|
| Core | Current Smoker | 7.9 | 3.39 |
|  | Non-current Smoker | 2.1 | 5.61 |
|  | True Rate | Se = 0.80 | Sp = 0.62 |
| Extended | Current Smoker | 9.61 | 1.36 |
|  | Non-current Smoker | 0.39 | 7.64 |
|  | True Rate | Se = 0.96 | Sp = 0.85 |

One goal of the present disclosure is to apply the core gene signature and the extended gene signature to determine whether the impact of switching to a heated tobacco product (HTP) could be detected using the signature. To facilitate this goal, data from the REX-EX-01 study was obtained. The REX-EX-01 study was an open-label, randomized, controlled, two-arm parallel group study that recruited 42 healthy smokers of both genders, aged between 23 and 65 years. It was conducted to compare smokers of conventional cigarettes to smokers who recently switched to an HTP (herein referred to as the Tobacco Heating System 2.1 (THS 2.1)) over 5 consecutive days. The study was conducted according to Good Clinical Practices (GCP) and was registered on ClinicalTrials.gov, with the identifier NCT01780714. Blood samples were stored in PAXgene tubes and were sent to AROS Applied Biotechnology AS (Aarhus, Denmark) where they were further processed and hybridized to Affymetrix Human Genome U133 Plus 2.0 GeneChips.

To test whether the gene signatures identified herein provide a sensitive and non-invasive tool for assessing the exposure-response in clinical trials, the signatures were applied to the THS 2.1 data to determine whether the switch to the HTP could be detected in the whole blood transcriptome after five days. The hypothesis of this study was that the whole blood transcriptome of smokers who switched to THS 2.1 resembles that of a former smoker more than that of a current smoker. Instead of characterizing the gene expression profile of an HTP user that is specific to five days of switching (e.g., by extracting the signature from the REX-EX-01 study data), it is desirable to identify a transcriptome-based exposure response signature that could also serve as an indicator of a longer term switching pattern. This was achieved by establishing the core gene signature and the extended gene signature, which were both able to distinguish current smoker samples from non-current smoker samples.

After a quality check was performed of the CEL files of the REX-EX-01 study, 16 and 18 files remained for the conventional cigarette smokers and the THS 2.1 users at Day 5, respectively. Table 5 below shows the prediction results on the REX-EX-01 samples for the core gene signature (top three rows) and for the extended gene signature (bottom three rows). For the extended gene signature, the individuals who remained on conventional cigarettes (current smokers) were mainly classified as current smokers (69%) while subjects who switched to THS 2.1 were mostly classified as non-current smokers (89%). For the core signature, the true rate for current smokers is the same (69%), and 78% of the subjects who switched to THS 2.1 were classified as non-current smokers. Thus, both the core and the extended gene signatures predict the samples obtained from HTP users to be those of non-current smokers.

TABLE 5

|  |  | Current Smoker | Switchers to THS 2.1 |
|---|---|---|---|
| Core | Current Smoker | 11 | 4 |
|  | Non-current Smoker | 5 | 14 |
|  | True Rate | Se = 0.69 | Sp = 0.78 |
| Extended | Current Smoker | 11 | 2 |
|  | Non-current Smoker | 2 | 16 |
|  | True Rate | Se = 0.69 | Sp = 0.89 |

The results shown in Table 5 are in line with an initial hypothesis that the blood transcriptome of subjects switching to an HTP begins to resemble that of a former smoker rather than a current smoker, despite the fact that there was no notable difference between THS 2.1 and conventional cigarettes in nicotine and cotinine exposure (data not shown).

Moreover, FIG. 5C plots boxplots of the posterior probabilities of a sample being classified as a current smoker from the LDA model on the REX-EX-01 data, and FIG. 5F plots boxplots of the prediction scores from the linear discriminant function on the REX-EX-01 data. A sample with a negative prediction score is classified as a current smoker, while a positive prediction score indicates a non-current smoker status.

Compared with gene signature that relies on measurements of a single gene, gene expression profiling provides a global and more complete view of the biological processes in normal and pathological situations. When the expression trends of multiple genes are taken together, it is also possible to derive a signature or a classifier for a given physiological state, from an exposure response to a disease state. While the primarily affected tissue offers a sample that more accurate represents the normal, exposed, or pathological state, it is often not realistic to classify subjects using tissue biopsies. Because of the ease of blood sampling using minimally invasive techniques, blood-based signatures hold great promise for biomarker discovery. In this study, two sets of whole blood-based biomarkers have been identified, either of which can serve as a signature for the body's response to smoking and can therefore be used as a strong predictor for a smoking status of an individual.

A gene that was strongly highlighted in this study is LRRN3. The expression of LRRN3 was increased in current smokers compared with non-current smokers. The expression was decreased significantly between days 0 and 5 in the blood of subjects who switched to an HTP, and remained constant in the blood of subjects who remained on the conventional cigarettes in the REX-EX-01 study. Thus, LRRN3 appears to be an important gene in both the core and the extended signatures for measuring the effect of switching from conventional cigarettes to an HTP. In an example, the gene signature as described includes only LRRN3 and no other gene, or includes LRRN3 in combination with any other gene. In particular, the gene signature that includes LRRN3 is able to detect the switch from conventional cigarette smoking to use of an HTP by demonstrating a decrease in LRRN3 expression between days 0 and 5 after the switch.

The systems pharmacology approach described herein allows for the construction of one or more robust whole blood based smoker gene signatures that could distinguish current smokers from non-current smokers. The core gene signature described herein is based on six genes, and the extended gene signature is based on the core gene signature plus an additional five genes. Both gene signatures have remarkable accuracy in predicting a smoker status of an individual, as assessed by both sensitivity and specificity scores. When applied to the samples from the REX-EX-01 study, the signatures identified the subjects that used THS 2.1 after five days as non-current smokers, based on whole blood transcriptome data. Therefore, the signatures described herein provide a sensitive and a specific tool for assessing the exposure response using minimally invasive sampling.

Figure 2:
FIG. 2 is a flowchart of a process for assessing a sample obtained from a subject.

FIG. 2 is a flowchart of a process 200 for assessing a sample obtained from a subject, according to an illustrative embodiment of the disclosure. The process 200 includes the steps of receiving a dataset associated with a sample, the dataset comprising quantitative expression data for LRRN3, CDKN1C, PALLD, SASH1, RGL1, and TNFRSF17 (step 202), and generating a score based on the received dataset, where the score is indicative of a predicted smoking status of a subject (step 204). In some embodiments, the dataset received at step 202 further comprises quantitative expression data for IGJ, RRM2, SERPING1, FUCA1, and ID3. In some embodiments, the dataset received at step 202 further comprises quantitative expression data for one or more of CLDND1, MUC1, GOPC, and LEF1.

The score generated at step 204 is a result of a classification scheme applied to the dataset, wherein the classification scheme is determined based on the quantitative expression data in the dataset. In particular, in the examples described herein, the classifier that was trained on the LDA model may be applied to the dataset received at 202 to determine a predicted classification for the individual.

The gene signatures described herein may be used in a computer-implemented method for assessing a sample obtained from a subject. In particular, a dataset associated with the sample may be obtained, and the dataset may include quantitative expression data for LRRN3, CDKN1C, PALLD, SASH1, RGL1, and TNFRSF17 for the core gene signature. A score may be generated based on the received dataset, where the score is indicative of a predicted smoking status of the subject. In particular, the score may be based on a classifier that was built using the LDA model approach described herein. The dataset may further comprise quantitative expression data for the additional markers IGJ, RRM2, SERPING1, FUCA1, and ID3, which are included in the extended gene signature. The dataset may further comprise quantitative expression data for one or more of CLDND1, MUC1, GOPC, and LEF1.

In some embodiments, the dataset includes any number of any subset of the set of markers LRRN3, CDKN1C, PALLD, SASH1, RGL1, TNFRSF17, IGJ, RRM2, SERPING1, FUCA1, ID3, CLDND1, MUC1, GOPC, and LEF1. One or more criteria may be applied to the markers to be included in a signature, such as including at least three (or any other suitable number) of LRRN3, CDKN1C, PALLD, SASH1, RGL1, and TNFRSF17, at least two (or any other suitable number) of IGJ, RRM2, SERPING1, FUCA1, and ID3, and at least one (or any other suitable number) of CLDND1, MUC1, GOPC, and LEF1. In general, any signature using a combination of these markers may be used without departing from the scope of the present disclosure.

In some embodiments, the genes in the signatures described herein are used in assembling a kit for predicting smoker status of an individual. In particular, the kit includes a set of reagents that detects expression levels of the genes in the gene signature in a test sample, and instructions for using the kit for predicting smoker status in the individual. The kit may be used to assess an effect of cessation or an alternative to a smoking product on an individual, such as an HTP.

Figure 3:
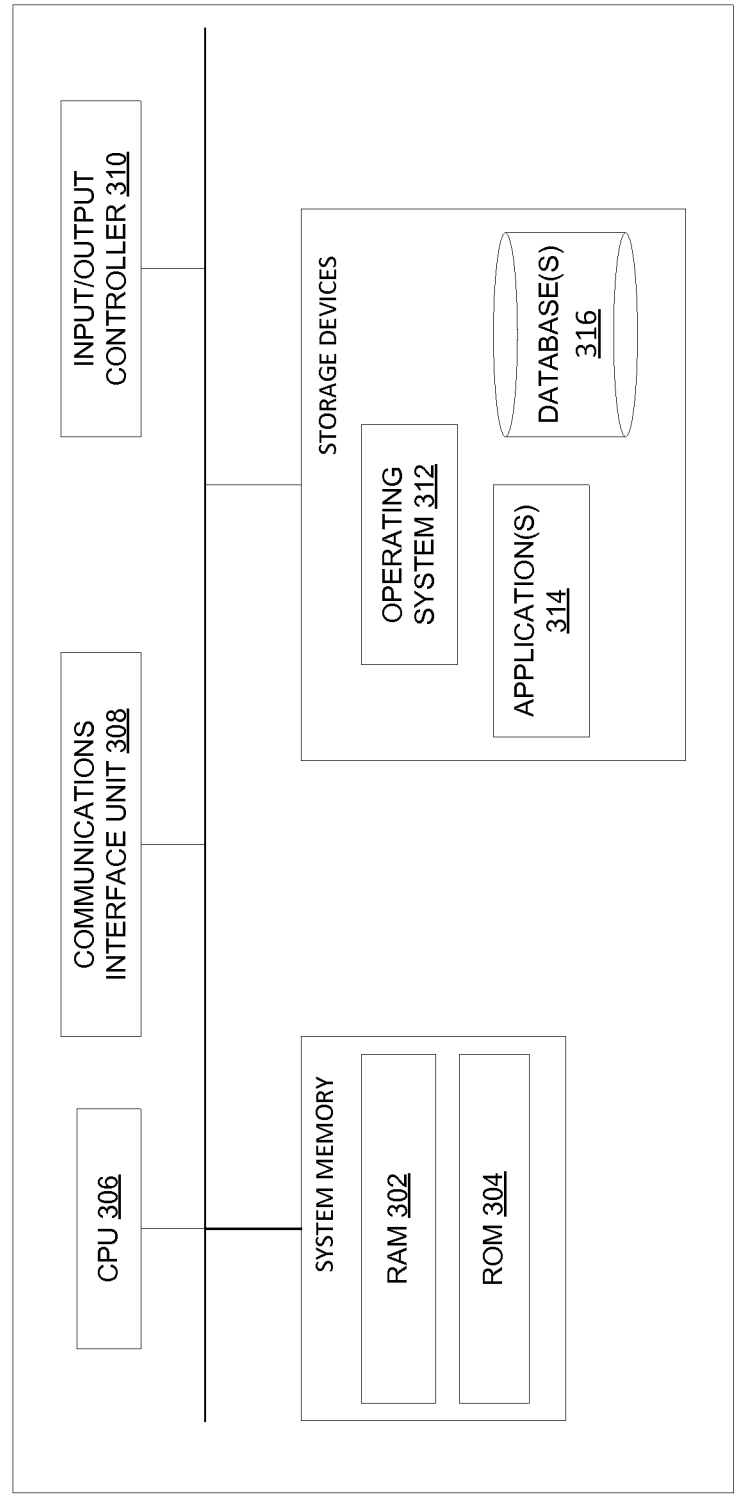
FIG. 3 is a block diagram of an exemplary computing device which may be used to implement any of the components in any of the computerized systems described herein.

FIG. 3 is a block diagram of a computing device for performing any of the processes described herein, such as the processes described in relation to FIGS. 1 and 2, or for storing the core gene signature, extended gene signature, or any other gene signature described herein. In particular, the gene signature that is stored on a computer readable medium includes expression data for LRRN3, CDKN1C, PALLD, SASH1, RGL1, and TNFRSF17. In another example, the computer readable medium includes a gene signature that includes expression data for at least five markers selected from the group consisting of: LRRN3, CDKN1C, PALLD, SASH1, RGL1, TNFRSF17, IGJ, RRM2, SERPING1, FUCA1, and ID3.

In certain implementations, a component and a database may be implemented across several computing devices 300. The computing device 300 comprises at least one communications interface unit, an input/output controller 310, system memory, and one or more data storage devices. The system memory includes at least one random access memory (RAM 302) and at least one read-only memory (ROM 304). All of these elements are in communication with a central processing unit (CPU 306) to facilitate the operation of the computing device 300. The computing device 300 may be configured in many different ways. For example, the computing device 300 may be a conventional standalone computer or alternatively, the functions of computing device 300 may be distributed across multiple computer systems and architectures. The computing device 300 may be configured to perform some or all of modeling, scoring and aggregating operations. In FIG. 3, the computing device 300 is linked, via network or local network, to other servers or systems.

The computing device 300 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 308 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 306 comprises a processor, such as one or more conventional microprocessors and one or more supplementary co-processors such as math co-processors for offloading workload from the CPU 306. The CPU 306 is in communication with the communications interface unit 308 and the input/output controller 310, through which the CPU 306 communicates with other devices such as other servers, user terminals, or devices. The communications interface unit 308 and the input/output controller 310 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 306 is also in communication with the data storage device. The data storage device may comprise an appropriate combination of magnetic, optical or semiconductor memory, and may include, for example, RAM 302, ROM 304, flash drive, an optical disc such as a compact disc or a hard disk or drive. The CPU 306 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 306 may be connected to the data storage device via the communications interface unit 308. The CPU 306 may be configured to perform one or more particular processing functions.

The data storage device may store, for example, (i) an operating system 312 for the computing device 300; (ii) one or more applications 314 (e.g., computer program code or a computer program product) adapted to direct the CPU 306 in accordance with the systems and methods described here, and particularly in accordance with the processes described in detail with regard to the CPU 306; or (iii) database(s) 316 adapted to store information that may be utilized to store information required by the program. In some aspects, the database(s) includes a database storing experimental data, and published literature models.

The operating system 312 and applications 314 may be stored, for example, in a compressed, an uncompiled and an encrypted format, and may include computer program code. The instructions of the program may be read into a main memory of the processor from a computer-readable medium other than the data storage device, such as from the ROM 304 or from the RAM 302. While execution of sequences of instructions in the program causes the CPU 306 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions as described herein. The program also may include program elements such as an operating system 312, a database management system and "device drivers" that allow the processor to interface with computer peripheral devices (e.g., a video display, a keyboard, a computer mouse, etc.) via the input/output controller 310.

The term "computer-readable medium" as used herein refers to any non-transitory medium that provides or participates in providing instructions to the processor of the computing device 300 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer may read.

Various forms of computer readable media may be involved in carrying one or more sequences of one or more instructions to the CPU 306 (or any other processor of a device described herein) for execution. For example, the instructions may initially be borne on a magnetic disk of a remote computer (not shown). The remote computer may load the instructions into its dynamic memory and send the instructions over an Ethernet connection, cable line, or even telephone line using a modem. A communications device local to a computing device 300 (e.g., a server) may receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Each reference that is referred to herein is hereby incorporated by reference in its respective entirety.

While implementations of the disclosure have been particularly shown and described with reference to specific examples, it should be understood by those skilled in the art that various changes in form and detail may be made therein without departing from the scope of the disclosure as defined by the appended claims. The scope of the disclosure is thus indicated by the appended claims and all changes which come within the meaning and range of equivalency of the claims are therefore intended to be embraced.

The invention claimed is:

1. A computer-implemented method for assessing a first sample obtained from a subject, comprising:
   receiving, by receiving circuitry, a first dataset associated with the first sample, the first dataset comprising first quantitative expression data for a gene signature comprising LRRN3, CDKN1C, PALLD, SASH1, RGL1, and TNFRSF17;
   generating, by a processor, a first score based on the first quantitative expression data for the gene signature by applying a classifier to the first quantitative expression data for the gene signature, wherein the classifier is trained based on a linear discriminant analysis (LDA) model computed based on the first quantitative expression data for the gene signature, and the first score is indicative of a first predicted smoking status of the subject;
   classifying, by the processor, the subject as a smoker based on the first predicted smoking status of the subject indicated by the first score;
   in response to the subject being classified as a smoker:
      administering to the subject a heated tobacco product for a five-day period after the first sample was obtained;
      receiving, by the receiving circuitry, a second dataset from a second sample obtained from the subject after the five-day period, the second dataset comprising second quantitative expression data for the gene signature; and
      generating, by the processor, a second score based on the second quantitative expression data for the gene signature by applying the classifier to the second quantitative expression data for the gene signature, wherein the second score is indicative of a second predicted smoking status of the subject and the second predicted smoking status indicates an effect of the heated tobacco product on the subject.

2. The computer-implemented method of claim 1, wherein first the quantitative expression data and the second quantitative expression data for the gene signature further comprise IGJ, RRM2, SERPING1, FUCA1, and ID3.

3. The computer-implemented method of claim 1, further comprising computing a fold-change value for each of LRRN3, CDKN1C, PALLD, SASH1, RGL1, and TNFRSF17 in the gene signature.

4. The computer-implemented method of claim 3, further comprising determining that each fold-change value satisfies at least one criterion that requires that each respective computed fold-change value exceeds a predetermined threshold for at least two independent population datasets.

5. A method, comprising:
   classifying a subject as a smoker based on a first gene signature;
   in response to the subject being classified as a smoker;
   administering to the subject a heated tobacco product for a five-day period after the subject was classified as a smoker;
   receiving, by receiving circuitry, a dataset associated with a sample, the dataset comprising quantitative expression data for a second gene signature comprising LRRN3, CDKN1C, PALLD, SASH1, RGL1, and TNFRSF17, wherein the sample was obtained from the subject after the five-day period; and
   generating, by a processor, a score based on the quantitative expression data for the second gene signature by applying a classifier to the quantitative expression data for the second gene signature, wherein the classifier is trained based on a linear discriminant analysis (LDA) model computed based on the quantitative expression data for the second gene signature, the score is indicative of a predicted smoking status of the subject, and the predicted smoking status indicates an effect of the heated tobacco product on the subject.

6. The method of claim 5, wherein the effect of the heated tobacco product on the subject is to make the predicted smoking status for the subject be a non-smoker.

* * * * *